US012569672B2

(12) United States Patent
Lombardo et al.

(10) Patent No.: US 12,569,672 B2
(45) Date of Patent: Mar. 10, 2026

(54) DEVICE, SYSTEM AND METHOD FOR TREATING A CORNEAL TISSUE

(71) Applicant: VISION ENGINEERING ITALY SRL, Rome (IT)

(72) Inventors: Giuseppe Lombardo, Rome (IT); Marco Lombardo, Rome (IT)

(73) Assignee: VISION ENGINEERING ITALY SRL, Rome (IT)

( * ) Notice: Subject to any disclaimer, the term of this patent is extended or adjusted under 35 U.S.C. 154(b) by 1121 days.

(21) Appl. No.: 17/618,894

(22) PCT Filed: Jun. 25, 2020

(86) PCT No.: PCT/IB2020/056002
§ 371 (c)(1),
(2) Date: Dec. 14, 2021

(87) PCT Pub. No.: WO2020/261163
PCT Pub. Date: Dec. 30, 2020

(65) Prior Publication Data
US 2022/0233842 A1     Jul. 28, 2022

(30) Foreign Application Priority Data

Jun. 27, 2019     (IT) ........................ 102019000010341

(51) Int. Cl.
*A61N 1/04*          (2006.01)
*A61F 9/00*          (2006.01)
*A61N 5/06*          (2006.01)

(52) U.S. Cl.
CPC .......... *A61N 1/0448* (2013.01); *A61F 9/0017* (2013.01); *A61N 5/062* (2013.01);
(Continued)

(58) Field of Classification Search
CPC .................. A61N 1/0448; A61N 5/062; A61N 2005/0626; A61N 2005/0648;
(Continued)

(56) References Cited

U.S. PATENT DOCUMENTS

2014/0336514 A1     11/2014  Peyman

FOREIGN PATENT DOCUMENTS

DE          102013007074 A1 *  10/2014
WO          2011116306 A2      9/2011
(Continued)

*Primary Examiner* — Theodore J Stigell
(74) *Attorney, Agent, or Firm* — Bayramoglu Law Offices LLC

(57)          ABSTRACT

A device for delivering a drug into a cornea is provided. The device includes a body having an internal cavity and a first aperture communicating with the internal cavity, wherein the first aperture is conformed to hermetically adhere to a periphery of a surface of the cornea; a second aperture to introduce the drug in the internal cavity, the device further includes a mask, supported by the body in correspondence of the first aperture, wherein, in operative condition, the first aperture adheres to a portion of the surface of the cornea, and the mask includes a plurality of through openings of opportunely variable size to achieve a corresponding variable spatial concentration of the drug across the cornea.

4 Claims, 9 Drawing Sheets

(52) U.S. Cl.
CPC ................. *A61F 2250/0069* (2013.01); *A61N 2005/0626* (2013.01); *A61N 2005/0648* (2013.01); *A61N 2005/0662* (2013.01)

(58) Field of Classification Search
CPC ........... A61N 2005/0662; A61F 9/0017; A61F 2250/0069
See application file for complete search history.

(56) References Cited

FOREIGN PATENT DOCUMENTS

| | | | |
|---|---|---|---|
| WO | 201295876 | A1 | 7/2012 |
| WO | 2012095876 | A1 | 7/2012 |
| WO | 2012158991 | A2 | 11/2012 |
| WO | WO-2015164626 | A2 * | 10/2015 |
| WO | 2016069628 | A1 | 5/2016 |
| WO | 2016191342 | A1 | 12/2016 |
| WO | 2017130043 | A1 | 8/2017 |

* cited by examiner

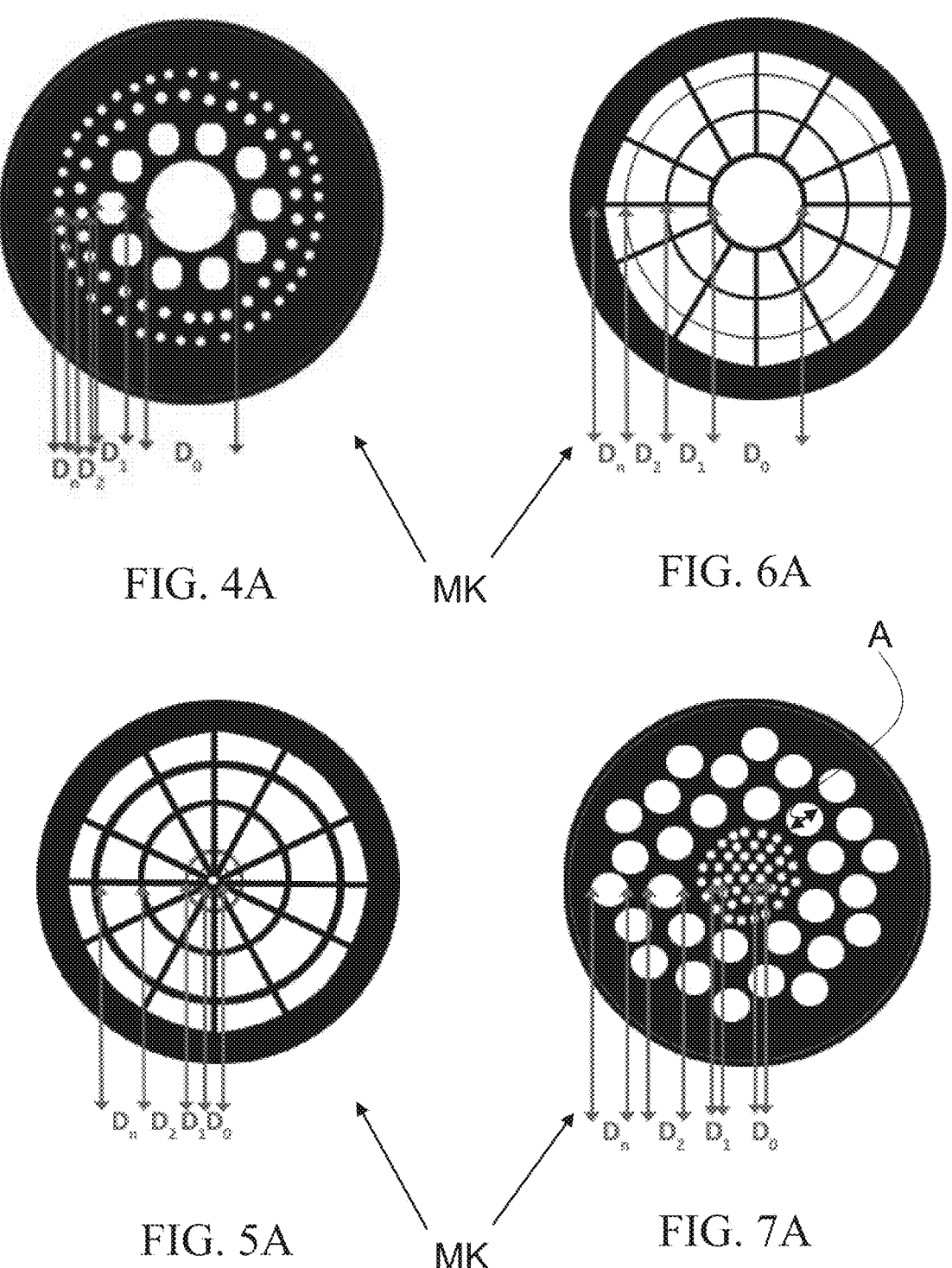
FIG. 4A     MK     FIG. 6A
FIG. 5A     MK     FIG. 7A

MK

MK

DEVICE, SYSTEM AND METHOD FOR TREATING A CORNEAL TISSUE

CROSS REFERENCE TO THE RELATED APPLICATIONS

This application is the national stage entry of International Application No. PCT/IB2020/056002, filed on Jun. 25, 2020, which is based upon and claims priority to Italian Patent Application No. 102019000010341 filed on Jun. 27, 2019, the entire contents of which are incorporated herein by reference.

TECHNICAL FIELD

The present invention relates to a device, system and method for treating a corneal tissue.

BACKGROUND

Refractive surgery is a surgical procedure aiming at improving the uncorrected visual acuity of the human eye, i.e., without using eye glasses or contact lens, by changing the focusing power of the optical components of the eye, such as the cornea or the lens. Several refractive surgical procedures have been used, some of which act onto the cornea and others onto the crystalline lens. Corneal laser vision correction procedures, such as photorefractive keratectomy (PRK), laser-in-situ keratomileusis (LASIK), femtosecond laser assisted LASIK, and the small incision lenticule extraction (SMILE) are the most used surgical techniques for improving uncorrected visual acuity. Unfortunately, these procedures may have severe adverse events.

In the last decade, riboflavin/UV-A corneal cross-linking has been increasingly used for stabilizing the biomechanical strength of the cornea weakened by disease, such as keratoconus, or laser corneal surgery. The corneal cross-linking is a minimally-invasive procedure, since it does not require for corneal incisions and, for this reason, it has been also termed as a "para-surgical" procedure. The mechanism of action of riboflavin/UV-A corneal cross-linking consists of generating additional covalent chemical ("cross-linking") bonds between the stromal proteins (i.e., collagen and proteoglycan core proteins) in order to improve the biomechanical strength and stability of the corneal tissue.

Recently, riboflavin/UV-A corneal cross-linking has been used as a stand-alone procedure for correcting low-grade myopia, i.e., defined by a myopic refraction of up-2 diopters, in healthy eyes.

The change of the focusing power of the cornea induced by riboflavin/UV-A corneal cross-linking is achieved by reinforcing the corneal tissue biomechanics, which in turn reshapes the anterior profile of the cornea. On the other hand, the change of the focusing power of the cornea induced by current riboflavin/UV-A corneal cross-linking techniques cannot be predicted or controlled. There are several methods for applying a photo-enhancer agent into the cornea through tissue incisions.

The document WO2016069628 discloses an apparatus, which includes an illumination system for illuminating, in a controlled way, a photo-enhancer agent administered into the cornea. Such apparatus includes a controller for defining mathematically both the three-dimensional distribution of the new covalent chemical bonds, which shall be induced between the stromal proteins to obtain the targeted biomechanical stiffening of the cornea, and the illumination parameters to efficiently illuminate the corneal tissue in order to achieve the targeted distribution of these new covalent chemical bonds between the stromal proteins. The additional covalent chemical bonds generated into the cornea are determined by the irradiation parameters of the light source, which is used to photo-activate the photo-enhancer agent into the cornea itself.

The document WO2016191342 relates to a system and method, which includes both a light source to photo-activate selectively a cross-linking agent administered into the cornea and a dosimeter, which measures the fluorescence emitted by riboflavin and provides information about the cross-linking activity.

The document WO2012158991 discloses a system for delivering a cross-linking agent into the cornea, whose photo-activation generates a biochemical reaction inducing new covalent chemical bonds between collagen proteins for reinforcing the biomechanics of the corneal tissue. The document does not propose any method for controlling the diffusion and distribution of the cross-linking agent into the corneal tissue.

The document WO2015164626 discloses an apparatus for administering a drug by using vacuum. The document does not propose any method for controlling the diffusion and distribution of the drug into the corneal tissue.

The document WO201295876 discloses another apparatus for administering a drug by electric current. The scope is to allow the drug penetration into the stroma through the intact corneal epithelium, which constitutes a barrier for molecules greater than 180 Dalton. The document does not propose any method for controlling the diffusion and distribution of the drug into the corneal tissue.

If not specifically excluded in the detailed description that follows, what is described in this chapter is to be considered as an integral part of the detailed description.

SUMMARY

The scope of the present invention is to improve or at least to disclose a device, system and method for treating a corneal tissue.

The technical task at the basis of the present invention is to soak a cornea with a cross-linking agent in a controlled and variable way across the corneal volume in order to achieve a precise correction of a predetermined amount of an optical aberration of the human eye. Specifically, upon defining a center of the cornea and a reference axis, variations in the administration of the agent can be controlled both along the radial and angular directions across the whole surface of the cornea.

Subsequently, the cornea is treated by means of a light radiation in order to photo-activate the cross-linking agent. The light radiation can be controlled in a way known from an expert of the technical field.

The differentiated application of the agent, according to the present invention, is obtained by masking the anterior surface of the corneal tissue.

In other words, a mask is applied and adhered onto the corneal tissue while the agent is administered.

The agent can be administered partly by masking and partly without masking the cornea.

In other words, a predetermined minimum level of concentration of the agent in the corneal stroma is desirable, while predetermined areas of the cornea are treated such they have a greater concentration of the agent based on the selective administration performed, according to the present invention, by masking the anterior surface of the cornea.

The amount of concentration of agent is managed by controlling the variation of the distribution of the shape and size of the through openings of the mask.

In a preferred embodiment of the invention, the penetration of the agent into the cornea is favored by simultaneously applying the vacuum to the cornea similarly to what disclosed in WO2015164626.

In another preferred embodiment of the invention, the penetration of the agent into the cornea is favored by corneal iontophoresis, which consists of applying an electric field similarly to what disclosed in WO201295876.

The present invention can be implemented both on explanted corneal segments and on an intact in situ cornea and consists of a non-invasive, nor tissue-threatening, treatment.

The device for delivering the cross-linking agent, object of the present invention, includes a support for supporting the said mask and at the same time for delimiting a reservoir for the agent, when an operatively lower part of the support is closed by a cornea to be treated.

In other words, the device, which is object of the present invention, includes a reservoir whose base is defined by the aforementioned mask. The reservoir is able to adhere to the corneal perimeter in a stable and hermetic way, and at the same time the mask adheres to a central portion of the cornea thus defining the differentiated penetration areas of the agent into the tissue.

According to a preferred variant embodiment of the invention, an upper base is operationally at atmospheric pressure, for example, when it is intended to favor the penetration of the agent by iontophoresis, as disclosed in WO201295876, or can be substantially closed and communicating with a vacuum pump, as disclosed in WO2015164626.

The overall shape of the delivery device is not particularly important, what matters is that under operative conditions, the delivery device is able to maintain the cross-linking agent in contact with the whole cornea masked and to administer the agent in a controlled and differentiated way into the corneal volume thanks to the interposition of the mask between the corneal surface and the agent.

According to a preferred variant embodiment of the invention, the delivery device defines, along its perimeter, a suction ring, which is able to create vacuum on an annular, peripheral, portion of the cornea, thus achieving a hermetic adhesion between the delivery device and the corneal surface itself.

According to a preferred variant embodiment of the invention, the suction ring has a first opening to create the suction, which is necessary to make the hermetic adhesion of the delivery device onto the corneal surface.

The delivery device can comprise a second opening, which is connected to a source for the administration of the cross-linking agent.

Thanks to the present invention, the corneal biomechanics can be changed in predetermined portions of the corneal tissue by the UV-A photo-activation of a cross-linking agent, which has been administered in a specific and personalized way, or by controlling its concentration and spatial distribution into the corneal tissue.

Cornea or corneal tissue are used in interchangeable way.

The present invention, according to any of the embodiments described above, also includes a system for a treatment, which in turn includes the aforementioned delivery device, means to facilitate the penetration or soaking of the agent, and a light source to photo-activate the agent. The light source can irradiate the corneal tissue either uniformly, i.e., with a uniform power density, or in a selective and specific way, i.e., with a variable power density across the cornea in order to photo-activate consequently the agent, whose concentration in the corneal tissue is distributed in a variable way by the delivery device.

Preferably, the system includes also means for measuring the concentration distribution of the cross-linking agent into the corneal volume before, during and at the end of treatment by means of the aforementioned light source or another source, and supervision and control means configured to estimate a corneal change on the basis of said concentration distribution, to control both means for distributing the cross-linking agent and the light source in order to achieve the targeted change of the cornea, which in turn corresponds to a predetermined correction of the focusing power of the eye.

An apparatus and method for monitoring and controlling has been disclosed in WO2017130043 and can be implemented within the scope of the present invention.

Thanks to this embodiment of the invention, it is possible to monitor and determine in real time riboflavin/UV-A corneal cross-linking treatment efficacy, being able to change the parameters for the administration of the cross-linking agent.

This makes possible to further modify in real time the parameters to photo-activate the cross-linking agent and accordingly to personalize the corneal reshaping in order to achieve the targeted improvement of the optical focusing power of the eye and/or the quality of vision.

Therefore, thanks to the present invention an additional degree of freedom is made available for the personalized corneal reshaping.

In addition, the present invention does not include any incision or pretreatment of the cornea to treat.

It is worth mentioning that, for the purpose of the present invention, the term "variable concentration" means the achievement of a predefined non-uniform concentration of the agent into a corneal tissue, such as to achieve the correct number of additional covalent chemical bonds between stromal proteins, which determines a predefined mechanical change of the cornea itself. Therefore, the term "variability" does not mean "random" but "predefined" as well as "variability" is in a selective meaning.

The claims describe the preferred embodiments of the invention, thus forming an integral part of this description.

BRIEF DESCRIPTION OF THE DRAWINGS

Additional scopes and advantages of the present invention will become more apparent from the following detailed description of a preferred, but non-exclusive, embodiment (and its variants) and of the approximate, and hence non-limiting, appended drawings, wherein:

FIGS. 4A-4C, 5A-5C, 6A-6C and 7A-7C illustrate some examples of the device according to preceding figures;

The same numbers and the same reference letters identify the same elements or components.

Figures 1, 2:
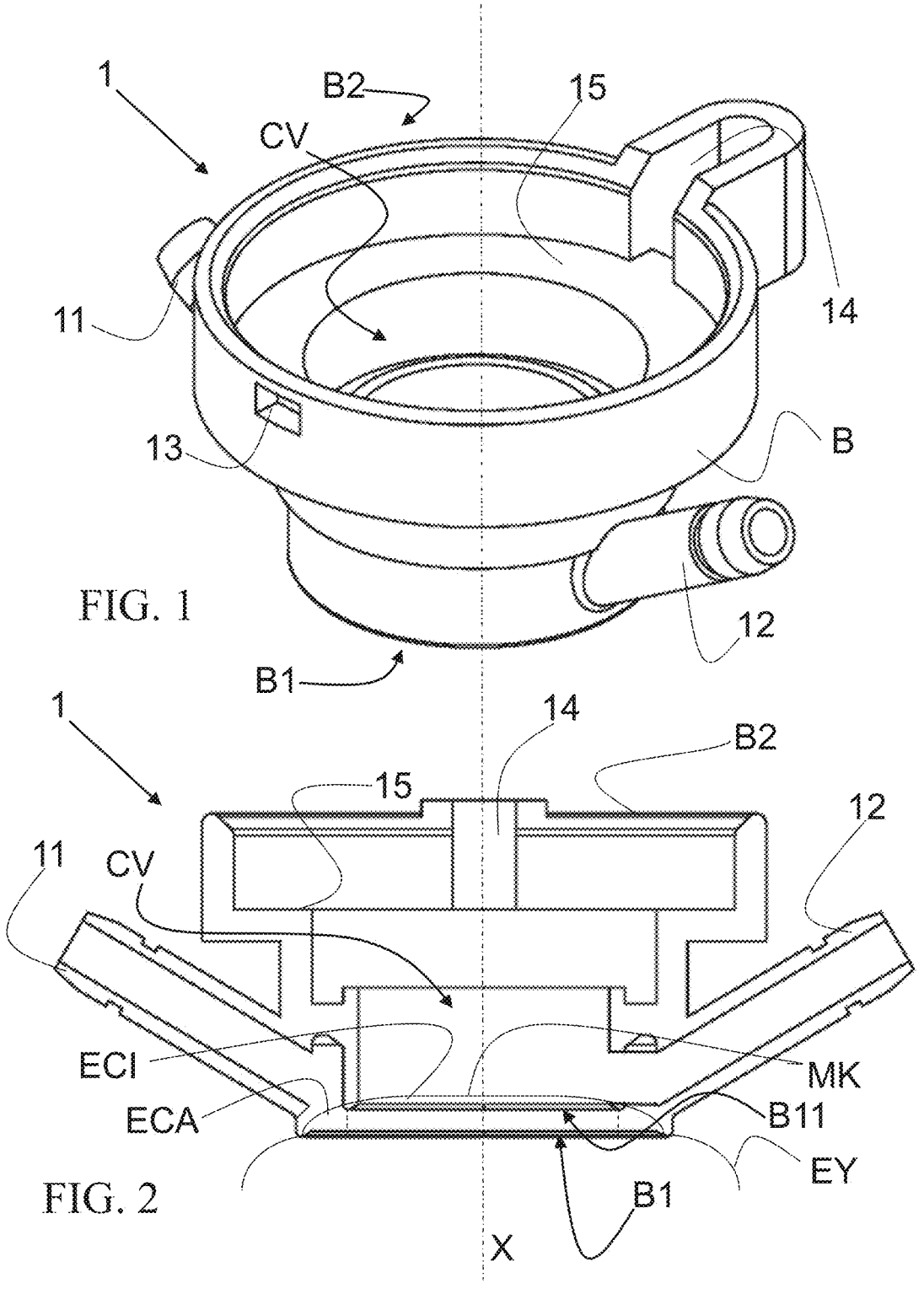
FIG. 1 illustrates a perspective view of a delivery device according to a preferred embodiment of the present invention.
FIG. 2 illustrates a longitudinal section of the device shown in FIG. 1 according to a plan, which comprises of symmetry axis of said device.

Within the scope of the present description, the term "second" component does not imply the presence of a "first" component. Said terms are indeed used as labels with the aim of improving the clarity of description and hence are non-limiting.

The elements and features illustrated in the preferred embodiments, including the drawings, can be combined between each other without leaving the scope of protection of the present application as described in the following.

DETAILED DESCRIPTION OF THE EMBODIMENTS

According to the present invention, it is intended to change the corneal biomechanics in predetermined portions of the corneal tissue by UV-A photo-activation of a cross-linking agent, which is selectively and precisely administered in order to achieve a predetermined shape change of the corneal profile.

In particular, according to the present invention, it is intended to achieve a variable spatial concentration of the cross-linking agent into a corneal tissue.

It is well known that if the cornea is properly shaped, it defines an optics, which is able to correct for the optical aberrations of the human eye.

The personalized and precise administration of the cross-linking agent allows to achieve a predetermined change of the corneal profile in order to correct for a refractive disorder, thus inducing a correction of the focusing power of the eye.

The riboflavin is a typical cross-linking agent.

In the following, for convenience, the cross-linking agent is termed simply as "agent" or "drug". Within the scope of the delivery device, it is not essential that the drug would be photo-activable, wherein within the scope of the system, which is object of the present invention, it is intended that the drug is photo-activable by a suitable light radiation.

The present invention can be implemented regardless of the type of agent, which is supposed to be a fluid and more specifically a liquid.

According to the present invention, the cornea to treat, either in situ or ex-vivo isolated in an eye bank, is soaked by an agent in a personalized way, by masking the anterior surface of the corneal portions that need little or no local modification.

According to the present invention, it is proposed a mask MK, which has through openings OP, which can vary in numbers, shape and size, either regarding to their relative distribution on the surface of the mask either along the radial or angular directions.

Examples of masks are shown in FIGS. 4A-4C, 5A-5C, 6A-6C, and 7A-7C, 8 and 14, which will be described in detail below.

A mask has a useful circular portion, which can deform or is previously deformed, adhering to a cornea to treat EC. Preferably, the whole mask has a shape of a thin disk.

As shown in the FIGS. 4A-4C, 5A-5C, 6A-6C and 7A-7C, the openings OP can have different distributions, shapes and sizes, and can consist of circular sections or circular holes or elliptic holes. Certainly there may be forms of openings that perform better than others, but the fundamental concept is that by distributing these openings appropriately, uniformly or non-uniformly, wider or narrower, it is possible to achieve a variable spatial concentration of the agent in the corneal tissue. This means that when the same areas of the cornea are exposed to a light source photo-activating the agent, this generates the said covalent chemical bonds proportionally to the local concentration of the agent. Therefore, the cornea presents a biomechanical response selectively differentiated between the treated areas with respect to non-treated areas according to the different spatial distribution of the agent's concentration. In other words, the cornea deforms so as to define a shaped lens suitable for correcting a predetermined visual disorder.

Figure 14:
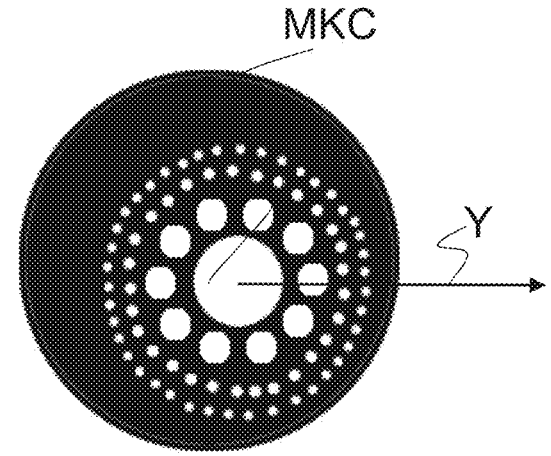
FIG. 14 illustrates an additional example of a portion of the device, which differs from similar portions in FIGS. 4A, 5A, 6A, and 7A.
Figure 15:
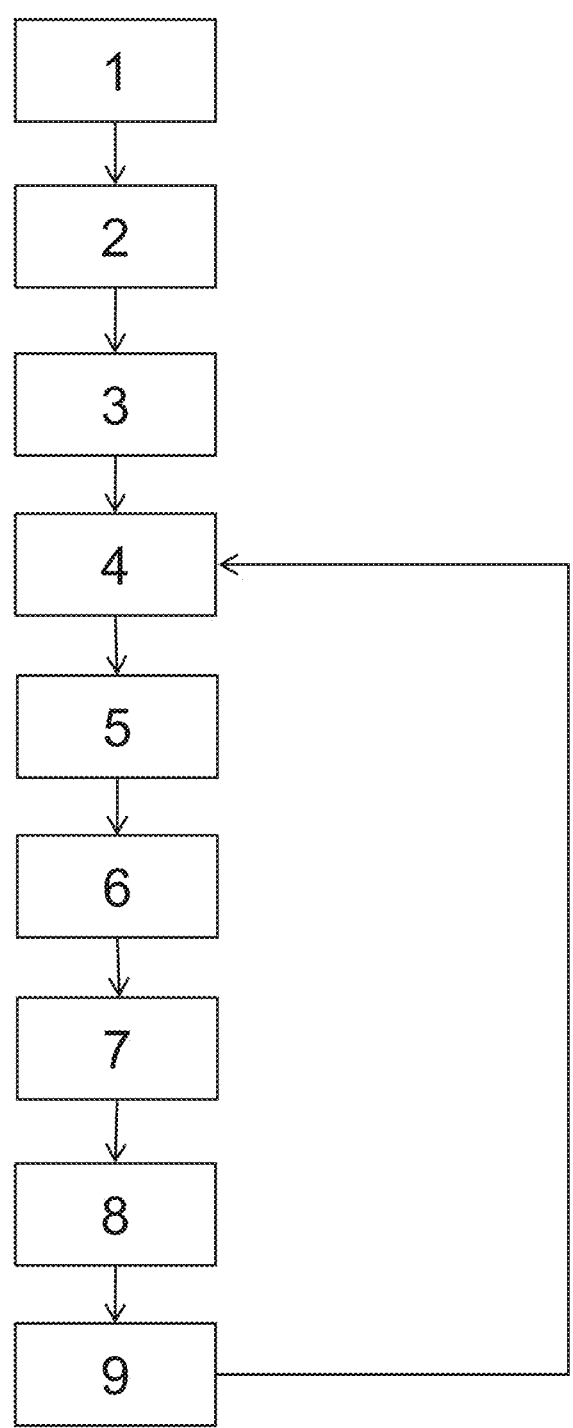
FIG. 15 illustrates a flow chart representative of a preferred method of operation of a system for treating a cornea according to the present invention.

By defining a reference Y axis passing through the disk centre MKC and lying in the plane identified by the disk itself MK, it is possible to differentiate the concentration of the agent by varying the distribution, shape and size of the openings either along the angular or radial directions. FIGS. 4A, 5A, 6A and 7A illustrate examples wherein the Y axis has its origin coincident with the centre MKC of the mask MK, while FIG. 14 illustrates an embodiment according to which the distribution of the openings' size varies radially with respect to the Y axis, which does not have origin in the centre MKC of the disk MK, since the centre of symmetry of the openings' distribution does not coincide with the centre of the disk defining the mask. This implies that the distribution of the openings' size is variable radially and angularly with respect to the centre MKC. Evidently, by differentiating the masking of the cornea, a different spatial distribution of the agent's concentration is achievable and therefore a different tissue mechanical effect induced by the photo-activation of the same agent.

The delivery device 1 composes of a body B, which has an internal cavity comprising an inferior open base B11 to which is associated or associable, along its perimeter, the said mask.

Therefore the base of the device can be arranged onto a cornea EC to treat and the internal cavity CV of the device communicates with said open base, defining a reservoir for the agent.

Under operative conditions, an axis perpendicular to the corneal surface is facing vertically with the convexity of the cornea facing upwards.

The device is associated with the cornea through said mask so that the same cornea closes the device's cavity inferiorly.

It is preferable that the inferior base would be circular in order to adapt as much as possible to the corneal shape.

Figure 8:
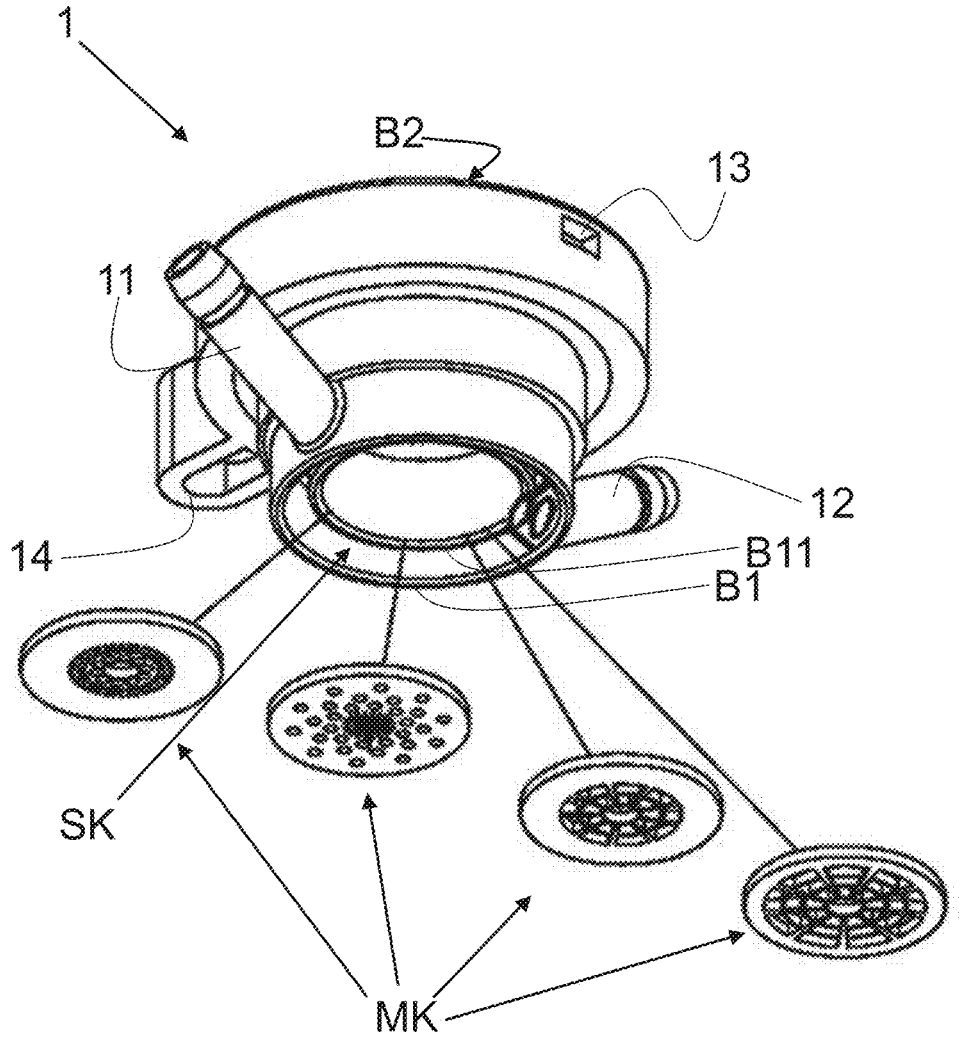
FIG. 8 illustrates the device of FIGS. 1-3 in a different perspective, exploded view with respect to FIGS. 1-3, putting in evidence the portion shown in FIGS. 4C-7C.

In addition, a seal between the device and the cornea is preferably achieved by a suction ring SK, as shown in FIG. 8, which is integrated in device 1 and is arranged along the perimeter of the mask MK. It can be delimited between the bases B11 and B1.

Therefore, at least a portion of the device 1, which is intended to interface with the cornea, has a rotational symmetry along the X axis, as shown in the figures, which coincides or is parallel with the axis perpendicular to the corneal surface.

FIG. 2 illustrates the device 1 associated with a corneal surface EY. The suction ring SK is comprised between the concentric bases B1 and B11 and is communicating with a suction port 11. Evidently the base B11 is more internal than cavity CV with respect to base B1.

Therefore, the two bases define two concentric boundaries to create the said suction ring, which is intended to generate a suction for sealing the device 1 to the peripheral portion of the cornea.

When the device is operatively associated with the corneal surface EY, the peripheral portion of the cornea ECA is slightly suctioned within the suction ring, while the central portion of the cornea ECI adheres to the mask MK.

The mask MK can be slightly deformable thus protruding into the internal cavity CV, or can be partially conformed to the cornea to treat.

It is convenient that the mask would be at least partially deformable in order to conform continuously to the variation of the corneal profile during treatment.

The mask MK can be realized with biocompatible materials, such as, for an approximate and non-exhaustive description, silicone, TPE (thermoplastic elastomers), TPV (vulcanized thermoplastic elastomers), PC (polycarbonate), ABS (acrylonitrile-butadiene-styrene), PVDF (polyvinyldenefluoride), PVC (polyvinyl chloride), teflon, polyethylene, and any other polymer that has a constant, flexible, non-adhesive chemo-physical structure and that can be conformed to the corneal profile.

According to a preferred embodiment of the present invention, in the delivery device 1, not shown, the mask is attached to a cylindrical body, which is internally sliding and lockable in the cavity CV so that the mask could be easily substituted without substituting the entire device 1.

The cylindrical body, for example, can be blocked into the cavity by means of a bayonet coupling or other means. In addition, it does not close the suction port 11, which is communicating with the suction ring arranged between bases B1 and B11.

In such case, the base B11 is defined by the same cylindrical body supporting the mask MK.

According to a preferred embodiment of the present invention, the internal cavity CV of the device is filled through a filling port 12 connected to an agent's reservoir. Alternatively, the agent can be administered manually through another aperture of the cavity CV.

The dosing time of the agent into the cornea is mainly dependent on the chemo-physical characteristics of the agent. For example, an optimal penetration can be obtained after at least 15 minutes of manual application, which is performed at atmospheric pressure and the absorption of the agent is obtained by the natural capillarity of the corneal tissue.

In order to hasten the penetration of the agent into the corneal tissue, iontophoresis or vacuum techniques can be used and the optimal concentration can be achieved within 5-15 minutes based on the technique and parameters used for administering the agent. Whereas for technique is intended the use of methods, which have been exhaustively described below in the text and are well known to the expert in the technical field, for facilitating the penetration of the agent.

To this end, the present delivery device can be modular in the sense that it includes fasteners, which provide means for inserting an electrode for iontophoresis or a cap with a second port for vacuum.

It is preferable that the cavity CV would have two opposing apertures, one to adhere with the cornea and the other to insert an electrode GR for iontophoresis or a cap 3 to implement the vacuum technique.

Figure 3:
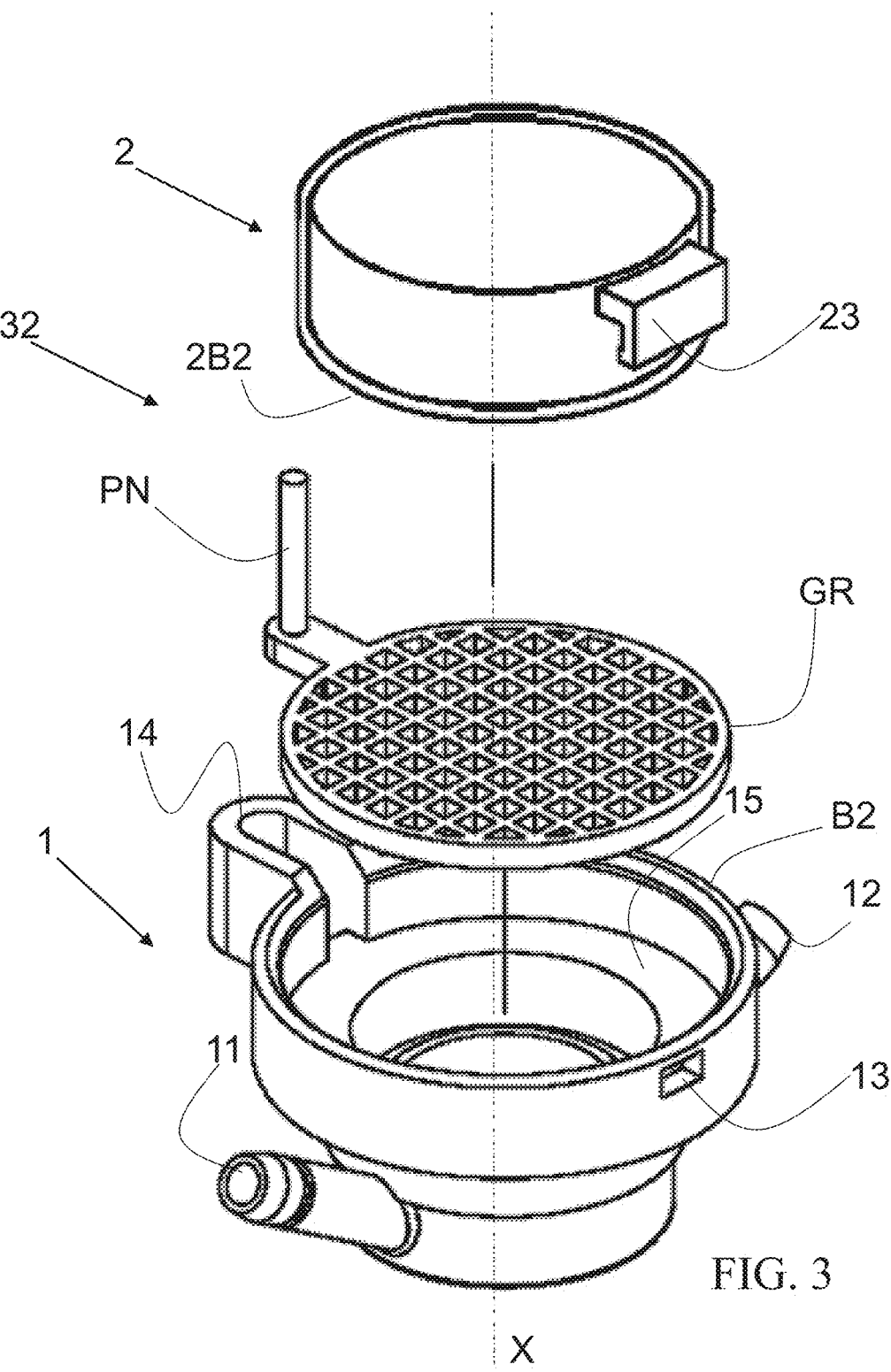
FIG. 3 illustrates a perspective exploded view according to a first operative configuration of the device of preceding FIGS. 1 and 2.

With reference to FIGS. 1, 2 and 3, the device has opening B2, which is circular and in the opposite side with respect to the bases B1 or B11.

In addition, internally, an annular, flat, abutment surface is arranged to support the electrode, which can be introduced through the aperture B2 until it is arranged onto the abutment surface 15. Subsequently, the electrode GR having preferably a circular shape of a flat grid is blocked by means of a cover 2, which is inserted at least partially into the cavity CV by pressing the grid onto the said surface 15.

This abutment surface lies on a plane perpendicular to the X axis of device 1.

The cover 2 has a clip element 23 that can be inserted, in locked operative conditions, into the aperture 13 of the body of device 1.

The grid of the electrode has a pin PN for the electrical connection to a reference potential generated by an external electric generator, not shown.

The pin is parallel to the X axis of symmetry of the device and protrudes sideways, so that also the device 1 can comprise preferably a site 14 that can accommodate such pin. The site 14 represents a lateral expansion of the cavity CV in correspondence of the abutment surface 15.

When the cover 2 is inserted into the cavity, the pin can be reached from above in order to be connected to said electric generator. Evidently, a second electrode can be connected directly or indirectly to the cornea so that it is in a sandwich configuration between the grid and the second electrode.

When an in situ treatment is performed, a second electrode, which has the function to be a passive return electrode, can be connected to either part of the body of a patient, for example, on the forehead in order to close the electrical circuit.

Vice versa, if the treatment is performed on an explanted human cornea, there would be no time constraint for dosing the agent and therefore there would be no advantage from utilizing techniques to facilitate the penetration of the agent into a corneal tissue.

When the administration of the agent is facilitated by means of iontophoresis, the cavity CV is filled at least to bath the grid GR so that it can generate an electrical field favoring the penetration of the agent into the corneal tissue, which is exposed to the openings of the mask.

Figures 9, 10:
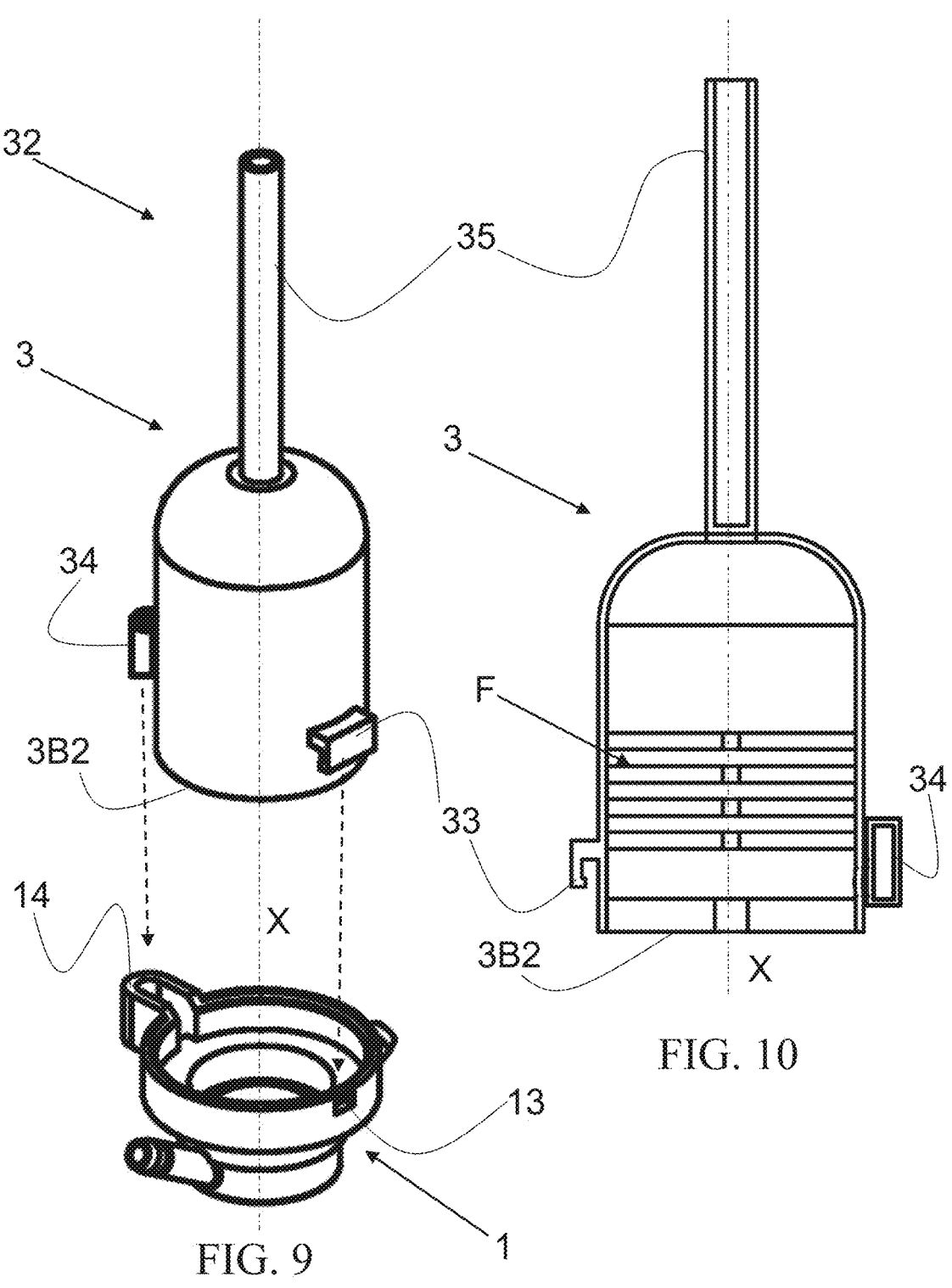
FIG. 9 illustrates a perspective exploded view according to a second operative configuration of the device of preceding FIGS. 1, 2 and 8.
FIG. 10 illustrates a longitudinal section of a second portion of the device in FIG. 9 according to the same section plane shown in FIG. 2, FIGS. 11-13 illustrate some examples of a system for treating a corneal tissue, which implements the aforementioned device.

With reference to FIGS. 9 and 10, it is illustrated a cap 3, which can be inserted into the cavity CV through the aperture B2, thus realizing a seal.

This cap 3 has a port 35 for the vacuum, which can be connected to a pump, not shown, in order to create vacuum into the cavity CV.

It preferably comprises a component 34, which is perfectly complementary to the site 14 of the device 1 and a clip element 13, which is complementary with the aperture 13.

It is therefore understood that the device 1 can be equipped or not with components that facilitate the penetration and dosing of the agent.

It is also understood that the present invention has a modular embodiment, which allows, in a unique body, to implement different techniques with the scope to facilitate the penetration and dosing of the agent into the ECI portion of the cornea to treat.

The portion ECI of the corneal surface is internal with respect to the peripheral and hermetic adhesion of the body B with the cornea.

Only for this reason, the cap 3 comprises the element 34, which serves to close the site 14 for the pin of the grid GR. On the other hand, if the vacuum technique is implemented, the grid GR is not included in the device, in other words, the two solutions for iontophoresis or vacuum are alternative and the device object of the present invention can be preferably modular allowing to use either techniques according to the specific need.

According to a preferred embodiment of the cap 3 for the vacuum, it has a hollow and tapering shape along the X axis of symmetry and internally has a filter F, which is arranged between the cavity and port 35 and has the function to prevent the agent to flow back through the port 35.

The filter can be of various types, for example it can be a labyrinth or it can include a spongy element with one or more pores or through openings.

FIGS. 4A, 5A, 6A and 7A in combination with FIGS. 3, 8 and 9 clarify that the device of the present invention is preferably completely modular either in terms of supporting the masks having different effects of masking, or in terms of means to favour the penetration of the agent into the corneal tissue.

The description of FIGS. 4B-7C is given in the following.

Figures 4B, 4C, 5B, 5C, 6B, 6C, 7B, 7C:
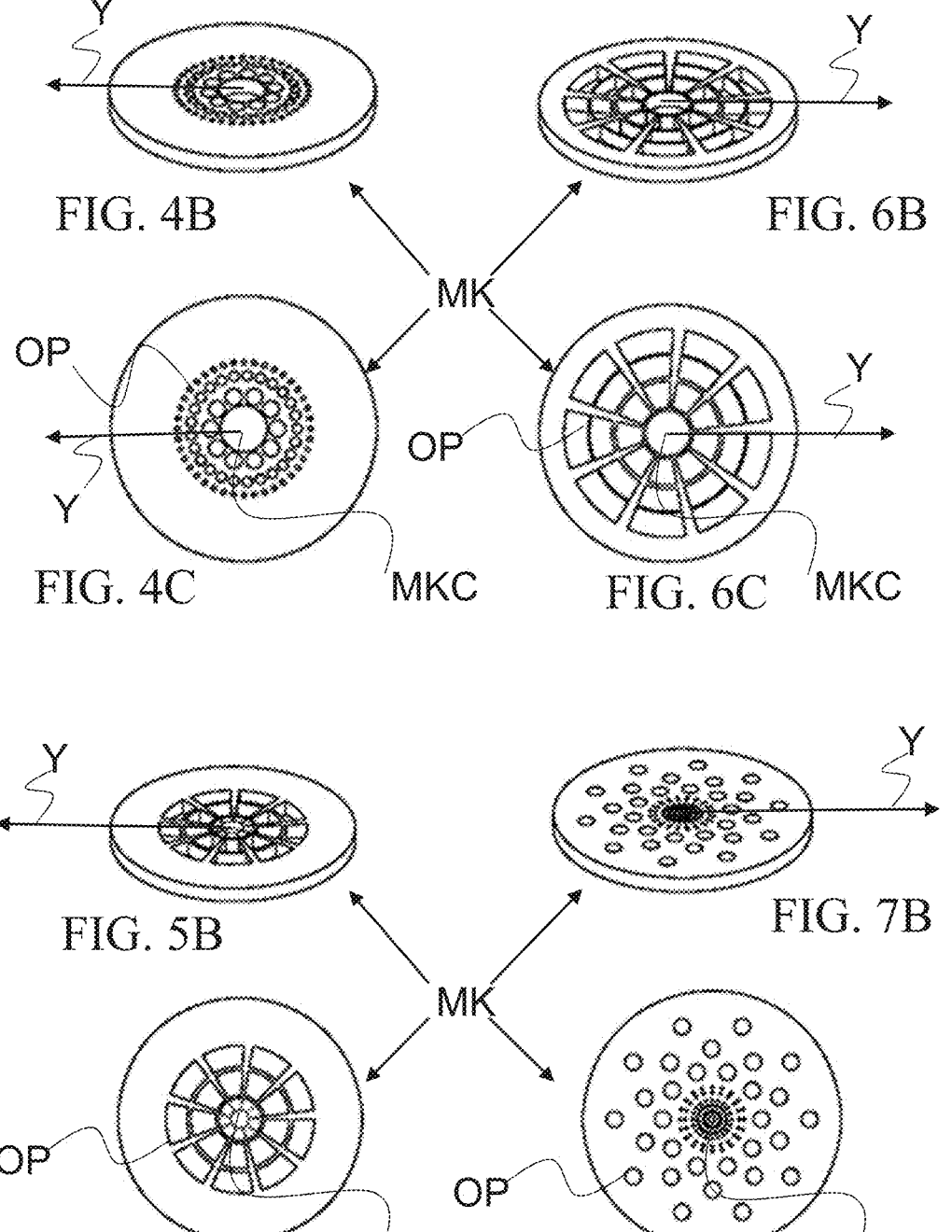

The pair FIGS. 4B and 4C illustrate a mask MK in a perspective and plan view respectively.

Similarly, the pair FIGS. 5B and 5C, 6B and 6C, and 7B and 7C illustrate the masks MK in a perspective and plan view respectively.

The masks of the pair FIGS. 4A and 6A are specifically designed to treat a myopic eye, with or without astigmatism, since they concentrate the larger openings in a central zone of the disk, these openings being narrower across the periphery of the mask.

The masks of the pair FIGS. 5A and 7A are specifically designed to treat a presbyopic and/or hyperopic eye, with or without astigmatism.

A certain number of radii, D0-Dn, can be defined, which taken in pairs identify as many circular rings, concentric and centered, in the case of FIGS. 4A, 5A, 6A and 7A, in the center of the disk defining the mask, each circular ring having constant radial width and the widths vary with the distance from the center. Within each ring there are present through openings, either circular, elliptical or as portions of circular sectors.

It should be taken into account that the masks of FIGS. 4A, 5A, 6A and 7A only represent examples of masks whose openings' distribution is center-symmetric, that is the center of symmetry is coincident with the center of the disk MKC, while FIG. 14 illustrates the center of symmetry of the openings' distribution that is different from the center MKC of the disk defining the mask. In this case, the distribution is "non-center symmetric" considering the center MKC as the center of the mask, but "center-symmetric" with respect to the origin of the Y axis. In addition, with respect to the origin of the Y axis there is a distribution of width of the openings that varies radially. However, other options either "center symmetric" or "non-center symmetric" wherein the distribution, shape and size of the single openings can vary along radial and angular directions.

It should be taken into account that it is not essential that the openings are distributed symmetrically with respect to a point of the mask.

The size of the openings and their distribution can be varied taking into account the targeted shape of the cornea to be achieved, starting from its original shape.

In addition, optical aberrations dependent on the Y axis can be corrected and therefore the distribution and width of the openings can vary also with respect to the Y axis, with reference to FIGS. 4C-7C.

Therefore, the number, size, shape and distribution of the openings OP are configured in such a way that the administration of the agent is personalized by dosing and distributing its concentration into the cornea stromal matrix and thus changing, after appropriate UV-A photo-activation of the agent, the dioptric power of the corneal tissue. In general, the amount of agent is greater than a threshold $C_{th}$ across the areas of the corneal tissue in which a greater amount of covalent chemical bonds between stromal proteins is to be generated by an appropriate UV-A light photo-activation; and the concentration is lower than a threshold $C_{th}$ across the areas of the cornea in which no additional amount of covalent chemical bonds between stromal proteins is to be generated or the agent shall not be photo-activated by the UV-A light, although it is desirable that the agent acts as a filter to attenuate the transmission of the light radiation towards the internal structures of the eye. In other words, concentrations of the agent above the threshold $C_{th}$ are useful to photo-activate, while concentrations of the agent below the threshold $C_{th}$ are useful only to protect the internal structures of the eye from UV-A light radiation.

Therefore, it can be useful to have a minimum concentration of the agent across the masked areas of the cornea. This concentration can be reached inside the corneal stroma either performing a partial administration of the agent, without any masking, or varying the size and distribution of the through openings, or by a combination of said solutions.

If the size of the openings of the mask of the administration reservoir, is narrower than a predetermined threshold $A_{th-1}$ (for example ≤0.2 mm diameter), the amount of the agent that penetrates into the corneal tissue is lower than the concentration threshold $C_{th}$ (for example ≤20 μg/cm$^3$). Therefore, the agent with concentration lower than $C_{th}$ has the sole function to protect the internal structures of the eye from the potential hazardous photo-toxic effect of the UV-A light radiation. On the other hand, if the size of the openings is greater than said predetermined threshold $A_{th-1}$, the amount of the agent that penetrates into the underlying areas of the corneal tissue is greater than $C_{th}$ and this amount is correlated with either the shape and/or the size of the openings as well as with the technique and the operative parameters of the active delivery device used. In addition, the larger the size of the opening, the more uniform is the distribution of the agent into the corneal tissue.

On the basis of some experiments, it has been found that the openings shall not have a size larger than a second threshold $A_{th-2}$ (for example ≥2 mm diameter), because it can alter the corneal epithelium (for example, causing de-epithelialization) during the administration of the agent with the vacuum technique, when a negative pressure gradient and/or a partial negative pressure is created in the underlying corneal tissue.

Therefore, the mask also creates a containing effect on the corneal epithelium that avoids the de-epithelialization due to the application of vacuum for facilitating the penetration of the agent into the corneal tissue.

In other words, a mask with through openings such as to allow a uniform distribution of the agent, that is in contrast with the scopes of the present invention, anyway produces a technical effect in combination with an administration of the agent performed by means of vacuum.

Therefore, openings with a size narrower than $A_{th-1}$, make sure that the amount of agent that penetrates into the corneal tissue is lower than the threshold $C_{th}$, instead for openings with size between $A_{th-1}$ and $A_{th-2}$, the concentration of the agent that penetrates into the corneal tissue is greater than $C_{th}$ and this amount is correlated either with the shape and/or size of the opening or with the delivery technique and operative parameters of the delivery device used.

Now, it is described a system for treating a cornea, which includes the device 1 described and exemplified above.

Figures 11, 12:
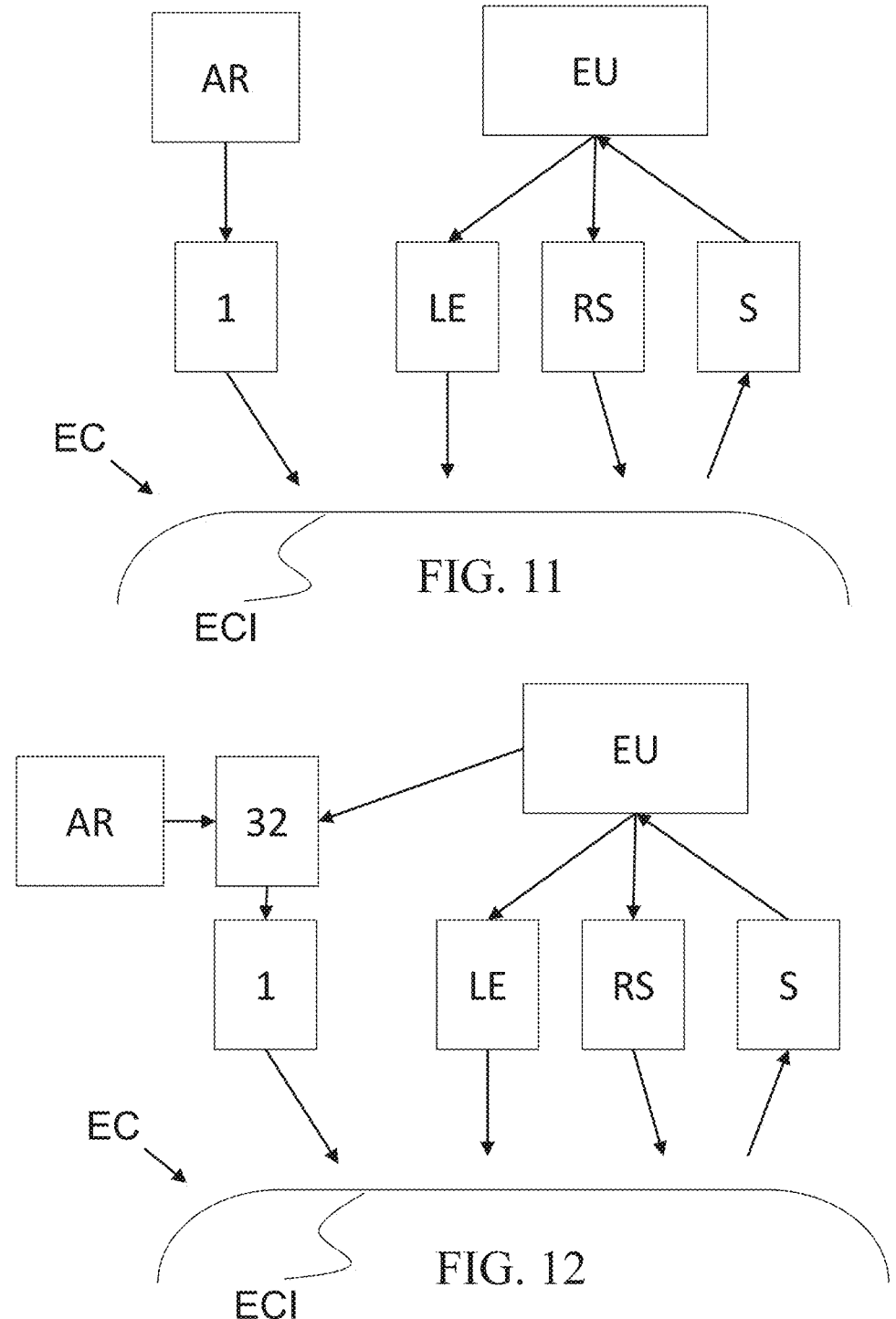

FIG. 11 illustrates a first example of a system for a treatment according to the present invention, which comprises:

a delivery device 1, a processing unit EU, one or more light sources LE, RS to illuminate the corneal tissue, means S for collecting a radiation reflected or emitted from the corneal tissue when undergoing said illumination.

The device 1 allows the administration of an agent contained in a reservoir AR of agent.

At the end of a procedure, albeit partial, for soaking the agent into the corneal tissue ECI, the processing unit controls the light source LE, RS that irradiates the cornea, with the aim to determine a spatial concentration distribution of an agent penetrated into the corneal tissue.

While the source LE is able to illuminate the cornea by photo-activating or not photo-activating the agent in relation to the density power of the light, the source RS is able to illuminate the cornea without activating the agent.

Nevertheless, in both cases is possible to obtain a feedback on the measure of the concentration distribution of the agent into the corneal tissue.

For example, the cornea can be illuminated with blue light by the source RS when the agent coincides with riboflavin. In this case, the sensor S is able to collect a blue light radiation reflected from the cornea.

Or the cornea can be illuminated by a UV-A light radiation by means of source LE and consequently sensor S is able to collect a radiation emitted from the agent penetrated into the corneal tissue and photo-excited by said UV-A light radiation. In the case of riboflavin, said radiation is green.

The UV-A light radiation can have an intensity lower than a threshold to photo-activate the agent, or can have an intensity greater than said threshold.

The signal collected by the sensor S is representative and indicative of the agent's concentration. It is evident that the light source/s and the sensor can be equipped with appropriate lenses and/or filters to manage the corresponding radiations.

The described system is similar to the content of document WO2017130043.

Unlike the above document, the present invention, does not aim to obtain a measure of the average concentration of the agent into the whole corneal volume, but intends to obtain a detailed map of the concentration distribution into the volume of the same cornea.

According to a first embodiment of the invention, the photo-activation is realized uniformly across the whole cornea.

According to a second embodiment, the photo-activation is realized selectively, that is non-uniformly, across portions of the whole volume of the cornea, taking into account an intentionally non-uniform distribution of the agent.

FIG. 12 shows a second preferred embodiment of the present invention in which the delivery device 1 is further equipped with means to facilitate 32 the penetration or absorption of the agent into the corneal tissue.

These means are generally indicated with the reference 32, but they can indicate either means for creating vacuum 3, see FIGS. 9 and 10, similarly to what has been described in WO2015164626, or means to perform iontophoresis GR, 2, see FIG. 2, similarly to what has been described in WO201295876.

According to a preferred embodiment of the invention, shown in FIG. 12, the processing unit EU is programmed to control also the means 32 facilitating the penetration or absorption of the agent into the cornea EC.

Figure 13:
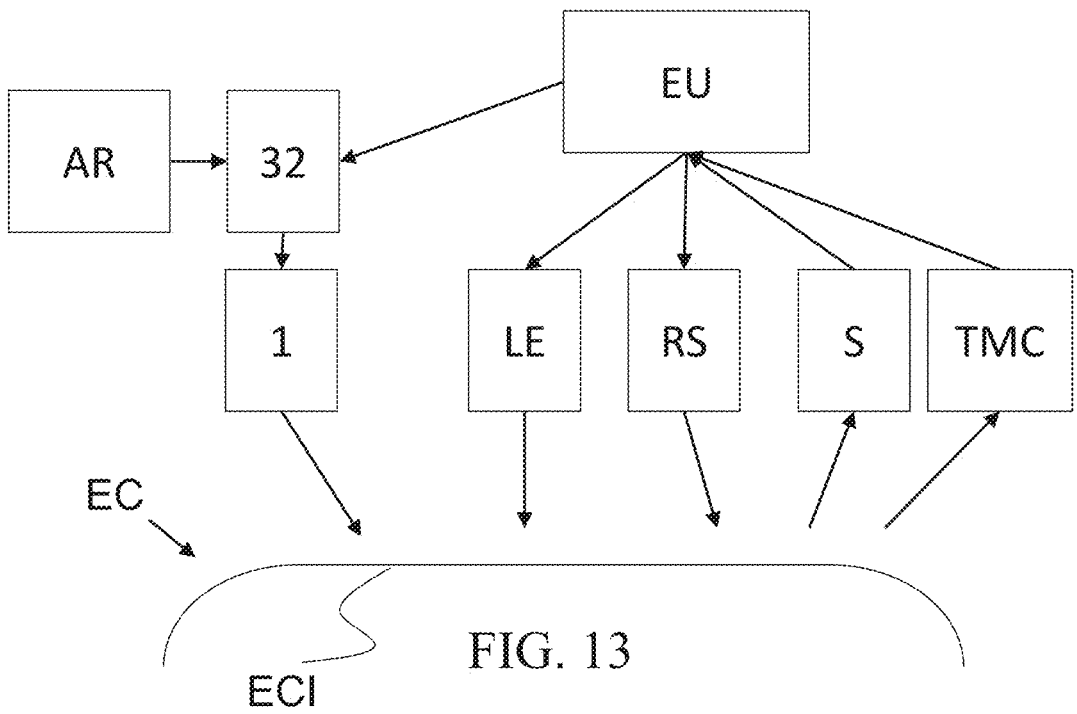

According to an additional preferred embodiment of the invention shown in FIG. 13, which can be combined with any of the preceding embodiments, the system is further equipped with a TMC unit of corneal topography or corneal/ocular aberrometer, which can measure the curvature and/or elevation of the corneal surfaces before, during and after the photo-activation of the cross-linking agent into the corneal tissue.

This unit TMC is also connected with the processing unit in order to provide it the preliminary information before the treatment of the cornea starts, and the feedback information in order to monitor the corneal changes induced by the administration of the agent and its corresponding photo-activation.

Preferably, the processing unit EU is programmed to acquire the information collected by the unit TMC corneal topographer/aberrometer and to compute a target corneal profile to achieve with the treatment.

Therefore, the processing unit EU computes an optimal spatial concentration distribution of the agent to administer into the corneal tissue and monitors the achievement of the optimal spatial distribution of the concentration of the agent into the corneal tissue, before the corresponding photo-activation, the variation of the agent's concentration during the photo-activation process, and the variation of the corneal profile by acquiring additional topographies or aberrometries.

In other words, the processing unit, thanks to the TMC unit of corneal topography or corneal/ocular aberrometry, determines a target corneal profile to achieve with the treatment.

The processing unit EU computes a target spatial concentration distribution of the agent into the corneal tissue and accordingly controls the means 32 until such spatial distribution is achieved. Alternatively, a skilled technician defines and sets into the processing unit the said target spatial concentration distribution of the agent and lets the system achieving such target distribution.

Subsequently the processing unit EU controls the source LE in order to photo-activate the agent and monitors, by means of sensor S, a variation of the agent into the corneal tissue and simultaneously monitors the evolution of change of the corneal profile by means of the TMC unit until the predetermined target profile is achieved.

A reduction of the agent's concentration into the cornea indicates that the agent has been photo-activated.

The processing unit comprises means of human-machine interface, for examples a monitor, a keyboard and preferably also a LCD touch screen and/or a trackball to allow the skilled technician to introduce the system settings.

When the processing unit computes the optimal spatial concentration distribution of the agent, it can indicate the most suitable mask.

Since multiple masks can be selected, the characteristics of the same mask can represent an additional input value, which is automatically computed or is manually set, to the processing unit with the aim to appropriately control means 32.

Preferably, the source of the first electro-magnetic radiation RS can generate a blue light radiation, while the sensor S includes a RGB camera or a hyperspectral camera, which is able to acquire the reflectance diffused or emitted from the cornea.

It is evident that the blue color depends on the selection of riboflavin as agent. Other agents could have a different absorbance spectrum and therefore the source could emit a radiation of different color.

Rather than using the said blue light source, the same light source LE could be used, that is intended for photo-activating the agent, to also monitor the agent's concentration. Indeed, by using a single source is possible, with irradiance powers greater than the activation threshold, to photo-activate the agent and at the same time to monitor the spatial concentration distribution of the agent into the corneal tissue, in combination with sensor S.

with irradiance powers lower than the activation threshold, to monitor the spatial concentration distribution of the agent into the corneal tissue, in combination with sensor S.

Filters and lenses can be used as needed by the skilled technician. More details on the methods to compute the concentration of the agent into the corneal tissue can be found in WO2017130043, here described for reference.

A biomechanical strengthening index, $K_{CXL}$, is defined, as described in document WO2017130043, which is calculated through a multiple linear regression algorithm, which models the relationship between the concentration value of the agent before its photo-activation, $C_0$, and the consumption of the agent during photo-activation, consumption %=$(C_0-C)/C_0$, where C is the concentration value during photo-activation. Specifically, values $C_0$ and C are to be intended as average values within the volume of the cornea to treat. Said index $K_{CXL}$, which is representative of the generation of additional chemical covalent bonds in the corneal stroma, can be appropriately used alone or in combination with a topographic index, $K_{topo}$, which is representative of the difference between the topographic map of the representative model of the cornea before treatment, chosen among one of the corneal topography map representations, which are well known by the skilled technician, and/or their combination, and a target representative model of the corneal shape to achieve with the treatment. The combination of the two indexes, said EFF, can be used to define additional cycles of administration and/or photo-activation until the procedure ends, when the treatment is stopped, that is when this index exceeds a predetermined threshold $EFF_{th}$. In other words, when said index exceeds said predetermined threshold, this means that the cornea achieved a topography congruent with the target model. Therefore, said index is substantially a comparison index among the corneal model acquired/developed before and during treatment and the target model to achieve with the treatment.

It is worthy highlighting that when the means 32 consist in the solution shown in FIG. 9, according to which the corneal tissue ECI is undergoing vacuum, it is possible to control the atmosphere inside cavity CV, for example by introducing, at least for a part of the treatment, specific gaseous substances other than the agent, with the aim of improving the penetration of the agent and/or improving the photo-polymerization process into the corneal tissue soaked with the agent.

The term "until to achieve" describes a feedback control, which therefore includes the steps of measuring a first variable and controlling a second as a function of the first one.

A system for treating a corneal tissue according the present invention, comprises of a device 1 according any of the embodiments described above.

Once the device 1 adheres to a cornea, the processing means are configured to perform the following steps:

(Step 1) acquisition of a first representative model of a corneal shape to treat, as per model is intended the acquisition of the volume and surface of the cornea to treat in metric form, this can be realized for example by using an optical coherence tomographer (OCT), a Brillouin microscopy, a Scheimpflug camera, a pachymeter and a corneal topographer;

(Step 2) acquisition or computation of a target model, which is representative of the corneal profile reshaped to correct for a predetermined optical aberration; the target corneal shape can be determined externally from the system, for example can be determined by a skilled technician or can be computed by the same processing means EU, as a function of an optical correction which is intended to apply to the in situ cornea of the eye to treat or to a cornea to graft;

(Step 3) computation of a number of covalent chemical bonds and their spatial distribution into the corneal tissue of the first model in order to induce the cornea to achieve the shape corresponding to the target model, and the following steps performed cyclically:

(Step 4) computation of a spatial concentration distribution of the drug into the cornea on the basis of said distribution of covalent chemical bonds;

(Step 5) computation of a distribution, shape and size of openings in a mask (MK) to achieve a selective administration of the drug such as to achieve said spatial concentration distribution of the drug;

(Step 6) control of said means facilitating (32) said penetration or absorption of the drug into the cornea on the basis of said concentration distribution, the control can be also a function of the distribution, shape and size of the through openings of the mask, indeed larger openings allow for a faster diffusion of the agent into the corneal tissue;

(Step 7) computation of an energy, power density and irradiance profile, uniform or variable, with which illuminating the cornea by means of the UV-A light source (LE) in order to achieve said distribution of covalent chemical bonds;

(Step 8) control of the source (LE) on the basis of said computed energy and power density; eventually, the source (LE) is also controlled within the irradiance profile on the basis of the selective distribution of the drug into the corneal tissue;

(Step 9) acquisition of an additional representative model of the cornea to treat and/or computation of an comparative index (EFF) of the treatment and stopping the method if said second model coincides with said target model and/or said comparative index exceeds the threshold $EFF_{th}$, or start again from said step (Step 4) computing the concentration distribution of the drug;

It is evident that the present method can include additional functional steps either for the treatment of the cornea or for monitoring the administration, distribution and consumption of the agent, caused by the photo-activation, as disclosed in WO2017130043.

The present invention can be advantageously carried out by a computer program, which comprises coding means for carrying out one or more steps of the method, when said program is run by a computer. Therefore it is intended that the scope of protection extends to that computer program and moreover to computer readable means, which comprise a recorded message, said computer readable means, comprising coding means, to realize one or more steps of the method, when said program is run in a computer.

There are possible variant embodiments to the non-limiting example described, without however leaving the scope of the protection of the present invention, including all the equivalent embodiments for a skilled technician, to the content of the claims.

From the above description, the expert in the field is able to realize the object of the invention without introducing additional constructive details.

What is claimed is:

1. A device for delivering a drug into a cornea, comprising a body, wherein the body comprises an internal cavity and a first aperture communicating with the internal cavity, wherein the first aperture is conformed or conformable to hermetically adhere to a perimeter of a corneal surface;

a second aperture to introduce the drug in the internal cavity, the device comprises a mask supported by the body at the first aperture and the mask is adapted, under operative conditions, to adhere to a portion of the corneal surface, preserving predetermined areas of the portion from a contact with the drug, wherein the mask comprises a biocompatible material disk comprising a plurality of through openings having opportunely variable size across the biocompatible material disk to achieve a corresponding variable spatial concentration of the drug across a corneal tissue;

wherein the body further comprises:

an upper side opposite the first aperture;

an internal annular abutment disposed within the internal cavity at the upper side; and a removable cover couplable to the upper side;

wherein a planar electrode grid is supported on the annular abutment when the cover is coupled.

2. The device according to claim 1, comprising a suction ring defined by a border of the first aperture and an external and concentric border with respect to the first aperture, and wherein the suction ring is conformed to adhere on an annular/peripheral zone of the cornea making the internal cavity hermetically connected with the corneal surface and wherein the body comprises a third aperture communicating with the suction ring to define a suction port.

3. The device according to claim 1, wherein the plurality of through openings have opportunely variable distribution in radial and/or angular terms with respect to a center of the biocompatible material disk and to a reference axis passing through the center of the biocompatible material disk and lying on the biocompatible material disk and/or the plurality of through openings have a variable shape.

4. The device according to claim 1, wherein the plurality of through openings with a size larger than a predetermined threshold are arranged in a proximal position with respect to a center to treat a myopic eye or are arranged in a distal position with respect to the center to treat a presbyopic/hyperopic eye.

* * * * *